United States Patent [19]
Dalbøge et al.

[11] Patent Number: 5,858,760
[45] Date of Patent: Jan. 12, 1999

[54] ENZYME WITH PECTIN LYASE ACTIVITY

[75] Inventors: Henrik Dalbøge, Virum; Lene Venke Kofod, Uggerløse; Markus Sakari Kauppinen, Copenhagen N; Lene Nonboe Andersen, Birkerød; Stephan Christgau, Vedbaek; Hans Peter Heldt-Hansen, Virum, all of Denmark

[73] Assignee: Novo Nordisk A/S, Bagsvaerd, Denmark

[21] Appl. No.: 887,365

[22] PCT Filed: Mar. 11, 1994

[86] PCT No.: PCT/DK94/00105

§ 371 Date: Sep. 26, 1995

§ 102(e) Date: Sep. 26, 1995

[87] PCT Pub. No.: WO94/21786

PCT Pub. Date: Sep. 29, 1994

Related U.S. Application Data

[63] Continuation of Ser. No. 513,928, Sep. 26, 1995, abandoned.

[30] Foreign Application Priority Data

Mar. 12, 1993 [DK] Denmark .................................. 0179/93
Oct. 28, 1993 [DK] Denmark .................................. 1216/93

[51] Int. Cl.⁶ ..................................................... C12N 9/88
[52] U.S. Cl. ................. 453/232; 435/254.11; 435/254.3; 435/252.3; 435/252.33; 435/320.1; 536/23.2; 536/23.74
[58] Field of Search .................. 435/232, 252.3, 435/252.33, 254.11, 254.3, 320.1; 536/23.2, 23.74

[56] References Cited

U.S. PATENT DOCUMENTS 5,103,883  4/1992  Viikari et al. ............................ 144/342
5,447,862  9/1995  Heim et al. ........................... 435/252.3

FOREIGN PATENT DOCUMENTS 0 278 355 A2   2/1988   European Pat. Off. .
0 353 188 A2   7/1989   European Pat. Off. .
0 439 997 A1  12/1990   European Pat. Off. .

OTHER PUBLICATIONS

Plastow et al., Symbiosis, vol. 2, pp. 115–122, 1986.
Somersen et al., Mol. Gen. Genet., vol. 234, pp. 113–120, 1992.
Gysler et al., Gene, vol. 89, pp. 101–108, 1990.
Alana et al, FEBS, vol. 280, No. 2, pp. 335–340, 1991.
Harmsen et al. "Cloning and Expression of a second *Asp. niger* . . . ", Curr. Genet., 18, 161–166, 1990.
Someren et al. "Structure of *Asp. niger* pelA gene and its exp. . . . ", Curr. Genet., 20, 293–299, 1991.
Gibriel et al. "Level of polygalacturonase, pectin estrase, pectin . . . ", Egypt J. Microbio, 189–198, 1983.

*Primary Examiner*—Robert A. Wax
*Assistant Examiner*—Nashaat T. Nashed
*Attorney, Agent, or Firm*—Steve T. Zelson, Esq.; Valeta Gregg, Esq.

[57] ABSTRACT

The nucleic acid sequence encoding a pectin lyase from *Aspergillus aculeatus,* CBS 101.43 and the corresponding amino acid sequence are disclosed. The nucleic acid is used to transform a host cell which is utilized in a method to make the pectin lyase. The catalytic properties and stability characteristics of the enzyme are reported. The enzyme is useful for the degradation of plant cell wall components.

11 Claims, 10 Drawing Sheets

ENZYME WITH PECTIN LYASE ACTIVITY

This application is a continuation of application Ser. No. 08/513,928 filed Sep. 26, 1995, now abandoned, which is a national application of PCT/DK94/00105 filed Mar. 11, 1994 which claims priority of Danish application Ser. Nos. 0179/93 filed Mar. 12, 1993 and 1216/93 filed Oct. 28, 1993, the contents of which are fully incorporated herein by reference.

FIELD OF INVENTION

The present invention relates to an enzyme with pectin lyase activity, a method of producing the enzyme, and an enzyme preparation containing the enzyme.

BACKGROUND OF THE INVENTION

Pectin polymers are important constituents of plant primary cell walls. They are composed of chains of 1,4-linked α-D-galacturonic acid and methylated derivatives thereof. The use of pectin-degrading enzymes is important for the food industry, primarily in fruit and vegetable processing such as fruit juice production or wine making, where their ability to catalyse the degradation of the backbone of the pectin polymer is utilised.

An assortment of different pectin degrading enzymes is known to be present in various microorganisms such as *Aspergillus niger*. Of these, pectin methylesterase catalyses the removal of methanol from pectin, resulting in the formation of pectic acid (polygalacturonic acid). Pectate lyase cleaves glycosidic bonds in polygalacturonic acid by β-elimination, pectin lyase cleaves the glycosidic bonds of highly methylated pectins by β-elimination, and polygalacturonase hydrolyses the glycosidic linkages in the polygalacturonic acid chain.

More specifically, pectin lyase may be used, alone or in combination with one or more other pectin degrading enzymes, in the production of fruit juice, in particular citrus juice, for partial or complete degradation of the pulp present in the juice after pressing.

For many purposes, it would be desirable to provide each of the pectin degrading enzymes present in, for instance, commercial preparations containing a number of different pectin degrading enzymes (an example of such a preparation is Pectinex Ultra SP®, prepared from *Aspergillus aculeatus*, available from Novo Nordisk A/S) in a form free from other components. In this way, it would be possible to produce enzyme preparations adapted to specific purposes, such preparations either containing a single pectin degrading enzyme or arbitrary combinations thereof. To serve this end, it is convenient to provide single-component pectin degrading enzymes by recombinant DNA techniques.

Plastow et al., *Symbiosis* 2, 1986, pp. 115–122, describe the cloning of four pectate lyase genes and one polygalacturonase gene from Erwinia in *E. coli*.

Cloning of a pectin lyase is described in EP 278 355 and EP 353 188.

M. Kusters-van Sommeren et al., *Mol. Gen. Genet.* 234, 1992, pp. 113–120, describe the nucleotide sequence of the *Aspergillus niger* pelB gene encoding pectin lyase B.

C. Gysler et al., *Gene* 89, 1990, pp. 101–108, describe the isolation and nucleotide sequence of the *Aspergillus niger* pelD gene encoding pectin lyase D.

A. Alaña et al., *FEBS Letters* 280, 1991, pp. 335–340, describe the purification and some characteristics of a pectin lyase from *Penicillium italicum*.

SUMMARY OF THE INVENTION

It is an object of the present invention to prepare single-component pectin lyases.

Accordingly, the present invention relates to an enzyme exhibiting pectin lyase activity, which enzyme is immunologically reactive with an antibody raised against a purified pectin lyase derived from *Aspergillus aculeatus*, CBS 101.43.

In the present context, the term "derived from" is intended not only to indicate a pectin lyase produced by strain CBS 101.43, but also a pectin lyase encoded by a DNA sequence isolated from strain CBS 101.43 and produced in a host organism transformed with said DNA sequence.

In another aspect, the invention relates to an enzyme exhibiting pectin lyase activity, which enzyme is encoded by a DNA sequence comprising at least one of the following partial sequences

| (a)  | CGATAAACTG | CAATATGGCA |      | (SEQ ID NO: 1)  |
|------|------------|------------|------|-----------------|
| (b)  | TTGACCACGA | TGGCTCAGGT |      | (SEQ ID NO: 2)  |
| (c)  | CTTTGGCCGT | TGGCCCAGCT |      | (SEQ ID NO: 3)  |
| (d)  | CGCCACAGCT | GTGAGTGTTT |      | (SEQ ID NO: 4)  |
| (e)  | CCGGTGCGGC | AGAGGGCTTC |      | (SEQ ID NO: 5)  |
| (f)  | GCAAAAGGTG | TCACTGGTGG |      | (SEQ ID NO: 6)  |
| (g)  | TGGTAGTGCG | ACTCCGGTTT |      | (SEQ ID NO: 7)  |
| (h)  | ATCTACCACG | ACTGATGAGC |      | (SEQ ID NO: 8)  |
| (i)  | TGGTCTCCTA | CCTCGGTGAC | TCTT | (SEQ ID NO: 9)  |
| (j)  | GCATTGTCAG | CGGTGCCAGC |      | (SEQ ID NO: 10) |
| (k)  | AATATTATCA | TTCAGAACGT |      | (SEQ ID NO: 11) |
| (l)  | CGCAATTACA | GATATCAACG |      | (SEQ ID NO: 12) |
| (m)  | AGAAATACGT | CTGGGGTGGT |      | (SEQ ID NO: 13) |
| (n)  | GATGCCATCA | CCCTCGACGA |      | (SEQ ID NO: 14) |
| (o)  | CGCCGATATG | GTCTGGATCG |      | (SEQ ID NO: 15) |
| (p)  | ACCATGTTAC | GACCGCCCGC |      | (SEQ ID NO: 16) |
| (q)  | ATCGGCCGCC | AGCACGTCGT |      | (SEQ ID NO: 17) |
| (r)  | CCTCGGCACA | AGCGCCGACA |      | (SEQ ID NO: 18) |
| (s)  | ACCGCGTCAC | CATCTCCAAC |      | (SEQ ID NO: 19) |
| (t)  | TCGTACTTCA | ACGGTGTCAC |      | (SEQ ID NO: 20) |
| (u)  | CAGTCACAGC | GCAACGTGTG | ACGG | (SEQ ID NO: 21) |
| (v)  | TTGTCGCAGT | CCGACACCGC |      | (SEQ ID NO: 22) |
| (w)  | TTTCTTGGTC | AACTTTGAAG |      | (SEQ ID NO: 23) |
| (x)  | GCAAGAATAT | GCGACCGTCG |      | (SEQ ID NO: 24) |
| (y)  | TCGGCGTACA | CGGCGATCAA |      | (SEQ ID NO: 25) |
| (z)  | GACTACGGTG | CCGAGTAACG |      | (SEQ ID NO: 26) |
| (aa) | CGGGCCAGGG | TAATCTCTGA |      | (SEQ ID NO: 27) |
| (bb) | GCGGTTGGCC | AGGCTCGAAG |      | (SEQ ID NO: 28) |
| (cc) | TATGCCTTAC | CCTGCCTGGT |      | (SEQ ID NO: 29) |
| (dd) | GGCAAGTAGC | ACTTGAGAGC |      | (SEQ ID NO: 30) |
| (ee) | TCACTGCAAC | GG         |      | (SEQ ID NO: 31) |

In a further aspect, the invention relates to an enzyme exhibiting pectin lyase activity, which enzyme is encoded by a DNA sequence comprising at least one of the following partial sequences

| CGATAAACTG | CAATATGGCA | TTGACCACGA | TGGCTCAGGT | CTTTGGCCGT |
|------------|------------|------------|------------|------------|
| TGGCCCAGCT | CGCCACAGCT | GTGAGTGTTT | CCGGTGCGGC | AGAGGGCTTC |
| GCAAAAGGTG | TCACTGGTGG | TGGTAGTGCG | ACTCCGGTTT | ATCTACCACG |
| ACTGATGAGC | TGGTCTCCTA | CCTCGGTGAC | TCTT;      | (SEQ ID NO: 32) |
| GCATTGTCAG | CGGTGCCAGC | AATATTATCA | TTCAGAACGT | CGCAATTACA |

-continued

| | | | | |
|---|---|---|---|---|
| GATATCAACG | AGAAATACGT | CTGGGGTGGT | GATGCCATCA | CCCTCGACGA |
| CGCCGATATG | GTCTGGATCG | ACCATGTTAC | GACCGCCCGC | ATCGGCCGCC |
| AGCACGTCGT | CCTCGGCACA | AGCGCCGACA | ACCGCGTCAC | CATCTCCAAC |
| TCGTACTTCA | ACGGTGTCAC | CAGTCACAGC | GCAACGTGTG | ACGG; |
| (SEQ ID NO: 33) | | | | |
| TTGTCGCAGT | CCGACACCGC | TTTCTTGGTC | AACTTTGAAG | GCAAGAATAT |
| GCGACCGTCG | TCGGCGTACA | CGGCGATCAA | GACTACGGTG | CCGAGTAACG |
| CGGGCCAGGG | TAATCTCTGA | GCGGTTGGCC | AGGCTCGAAG | TATGCCTTAC |
| CCTGCCTGGT | GGCAAGTAGC | ACTTGAGAGC | TCACTGCAAC | GG (SEQ ID NO: 34) | or a sequence homologous thereto encoding a polypeptide with pectin lyase activity.

In particular, the enzyme is encoded by the DNA sequence shown in the Sequence Listing as SEQ ID NO: 35 or a sequence homologous thereto encoding a polypeptide with pectin lyase activity.

In the present context, the term "homologue" is intended to indicate a polypeptide encoded by a DNA sequence which is at least 75% homologous to the sequence shown above encoding the pectin lyase of the invention, such as at least 80%, at least 85% at least 90% or even at least 95% homologous to any of the sequences shown above. The term is intended to include modifications of the DNA sequence shown above, such as nucleotide substitutions which do not give rise to another amino acid sequence of the pectin lyase, but which correspond to the codon usage of the host organism into which the DNA construct is introduced or nucleotide substitutions which do give rise to a different amino acid sequence and therefore, possibly, a different protein structure which might give rise to a pectin lyase mutant with different properties than the native enzyme. Other examples of possible modifications are insertion of one or more nucleotides into the sequence, addition of one or more nucleotides at either end of the sequence, or deletion of one or more nucleotides at either end or within the sequence.

DETAILED DESCRIPTION OF THE INVENTION

The enzyme of the invention may be isolated by a general method involving cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any pectin lyase activity of the enzyme produced by such clones.

A more detailed description of this screening method is given in Example 1 below.

The DNA sequence coding for the enzyme may for instance be isolated by screening a cDNA library of *Aspergillus aculeatus*, e.g. strain CBS 101.43, publicly available from the Centraalbureau voor Schimmelcultures, Delft, NL, and selecting for clones expressing the appropriate enzyme activity (i.e. pectin lyase activity as defined by the ability of the enzyme to cleave the glycosidic bonds of highly methylated pectin by β-elimination). The appropriate DNA sequence may then be isolated from the clone by standard procedures, e.g. as described in Example 1. It is expected that DNA encoding a homologous enzyme may be isolated by similarly screening a cDNA library of another microorganism, in particular a fungus, such as a strain of an Aspergillus sp., in particular a strain of *A. aculeatus* or *A. niger*, a strain of a Trichoderma sp., in particular a strain of *T. harzianum* or *T. reesie*, a strain of a Fusarium sp., in particular a strain of *F. oxysporum*, or a strain of a Humicola sp.

Alternatively, the DNA coding for a pectin lyase of the invention may, in accordance with well-known procedures, conveniently be isolated from DNA from any of the above mentioned organisms by use of synthetic oligonucleotide probes, prepared on the basis of a DNA sequence disclosed herein. For instance, a suitable oligonucleotide probe may be prepared on the basis of any of the partial nucleotide sequences (a)–(ee) listed above (cf. Sambrook et al., *Molecular Cloning. A Laboratory Manual*, Cold Spring Harbor, N.Y., 1989).

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the pectin lyase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the pectin lyase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed pectin lyase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified pectin lyase may be employed for immunization of animals for the production of antibodies. More specifically, antiserum against the pectin lyase of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4$)$_2SO_4$), followed by dialysis and ion exchange chromatography, e.g. on DEAE-Sephadex. Immunochemical characterization of proteins may be done either by Outcherlony double-diffusion analysis (O. Outcherlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

In a still further aspect, the present invention relates to an enzyme preparation useful for the degradation of plant cell wall components, said preparation being enriched in an enzyme exhibiting pectin lyase activity as described above.

The enzyme preparation according to the invention is preferably used as an agent for degradation or modification of plant cell walls. At present, degradation of plant cell walls is the most preferred use of the pectin lyase according to the invention, due to the high plant cell wall degradation activity.

The enzyme preparation may also comprise one or more other enzymes capable of degrading plant cell wall components, such as a pectate lyase, galactanase, pectin methylesterase, xylanase, glucanase, arabinanase, pectin acetylesterase, rhamnogalacturonase, polygalacturonase or polygalacturonase.

The invention is described in further detail in the following examples which are not in any way intended to limit the scope of the invention as claimed.

BRIEF DESCRIPTION OF THE DRAWINGS

The invention is further illustrated with reference to the appended drawings, wherein.

MATERIALS AND METHODS

Donor organism: mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prc1::HIS3; prb1:: LEU2; cir+).

Figure 1:
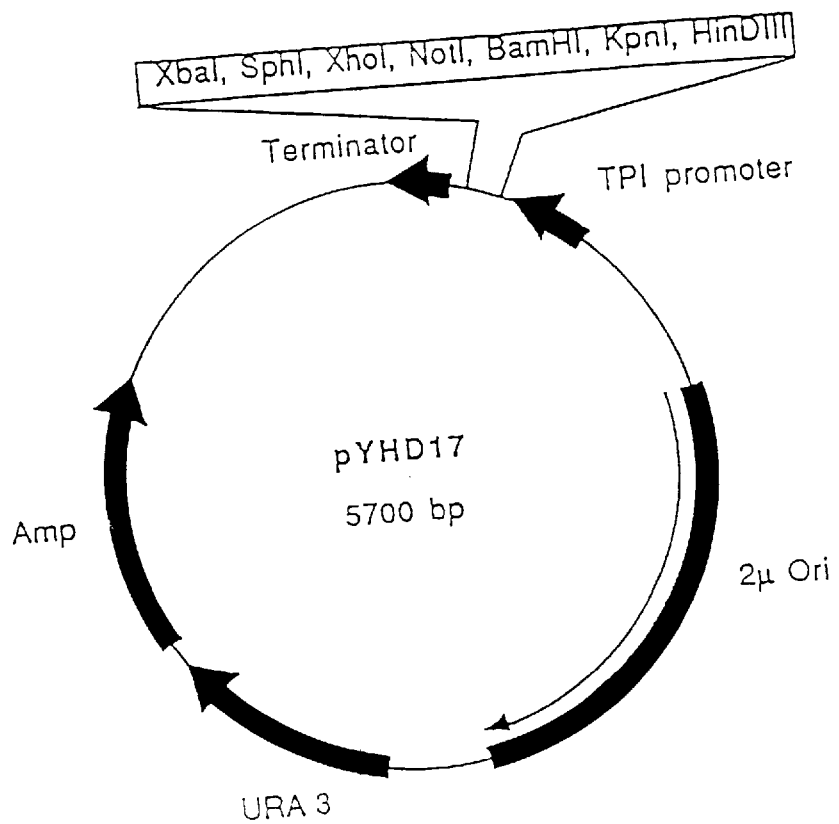
FIG. 1 shows the plasmid pYHD17.

Construction of an expression plasmid: The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Ball exonuclease treatment followed by addition of a SphI linker. Finally, an EcoRI linker was added at position—10. After these modifications, the promoter is included in a SphI-EcoRI fragment. Its efficiency compared to the original promoter appears to be unaffected by the modifications. The resulting plasmid pYHD17 is shown in FIG. 1.

Preparation of RNase-free glassware, tips and solutions: All glassware used in RNA isolations was baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA: The total RNA was prepared by extraction with guanidinium thiocyanate followed by ultracentrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GUSCN, 0.5% Na-laurylsarcosine, 25 mM Na-citrate, pH 7.0, 0.1M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25 000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 μl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)+RNA: The poly(A)+ RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1M NaCl, 1 mM EDTA, 0.1% SDS), followed by elution of the poly(A)+ RNA with 3 vols of elution buffer (10 mM Tris-Cl, pH 7.6, 1 mM EDTA, 0.05% SDS) preheated to +65° C., by collecting 500 $\mu$l fractions. The $OD_{260}$ was read for each collected fraction, and the mRNA containing fractions were pooled and ethanol precipitated at −20° C. for 12 h. The poly(A)+ RNA was collected by centrifugation, resuspended in DEPC-DIW and stored in 5–10 $\mu$g aliquots at −80° C.

Northern blot analysis: The poly(A)+ RNAs (5 $\mu$g/sample) from various mycelia were electrophoresed in 1.2 agarose-2.2M formaldehyde gels (Sambrook et al., 1989) and blotted to nylon membranes (Hybond-N, Amersham) with 10×SSC (Sambrook et al., 1989) as transfer buffer. Three random-primed (Sambrook et al., supra) $^{32}$P-labeled cDNA probes were used in individual hybridizations: 1) a 1.3 kb Not I-Spe I fragment for polygalacturonase I from *A. aculeatus* (described in Danish Patent Application DK 1545/92), 2) a 1.3 kb Not I-Spe I fragment encoding endoglucanase I from *A. aculeatus* (described in DK 0419/92) and 3) a 1.2 kb Eag I fragment for galactanase I from *A. aculeatus* (described in WO 92/13945). Northern hybridizations were carried out in 5×SSC (Sambrook et al., 1989), 5×Denhardt's solution (Sambrook et al., 1989), 0.5% SDS (w/v) and 100 $\mu$g/ml denatured salmon sperm DNA with a probe concentration of approx. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA synthesis:

First strand synthesis: Double-stranded cDNA was synthesized from 5 $\mu$g of *A. aculeatus* poly(A)+ RNA by the RNase H method (Gubler & Hoffman 1983, Sambrook et al., 1989) using the hair-pin modification. The poly(A)+RNA (5 $\mu$g in 5 $\mu$l of DEPC-treated water) was heated at 70° C. for 8 min., quenched on ice, and combined in a final volume of 50 $\mu$l with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 $\mu$g of oligo(dT)$_{12-18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second strand synthesis: After synthesis 30 $\mu$l of 10 mM Tris-Cl, pH 7.5, 1 mM EDTA was added, and the mRNA:cDNA hybrids were ethanol precipitated for 12 h at −20° C. by addition of 40 $\mu$g glycogen carrier (Boehringer Mannheim) 0.2 vols 10M NH$_4$Ac and 2.5 vols 96% EtOH. The hybrids were recovered by centrifugation, washed in 70% EtOH, air dried and resuspended in 250 $\mu$l of second strand buffer (20 mM Tris-Cl, pH 7.4, 90 mM KCl, 4.6 mM MgCl2, 10 mM (NH$_4$)$_2$SO$_4$, 16 $\mu$M $\beta$NAD$^+$) containing 100 $\mu$M each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) cDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and resuspended in 30 $\mu$l of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 $\mu$l 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds cDNA was blunt-ended with T4 DNA polymerase in 50 $\mu$l of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection: After the fill-in reaction the CDNA was ligated to non-palindromic BstX I adaptors (1 $\mu$g/$\mu$l, Invitrogen) in 30 $\mu$l of ligation buffer (50 mM Tris-Cl, pH 7.8, 10 mM MgCl2, 10 mM DTT, 1 mM ATP, 25 $\mu$g/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction and screening of CDNA libraries: The adapted, ds cDNA was recovered by centrifugation, washed in 70% EtOH and resuspended in 25 ml DIW. Prior to large-scale library ligation, four test ligations were carried out in 10 $\mu$l of ligation buffer (same as above) each containing 1 $\mu$l ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either PYES 2.0 vector Invitrogen or yHD13). The ligation reactions were performed by incubation at +16° C.

for 12 h, heated at 70° C. for 5 min, and 1 μl of each ligation electroporated (200 Ω, 2.5 kV, 25 μF) to 40 μl competent *E. coli* 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h, 50 μl plated on LB+ampicillin plates (100 μg/ml) and grown at +37° C. for 12 h.

Using the optimal conditions a large-scale ligation was set up in 40 μl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 μl DIW. One μl aliquots were transformed into electrocompetent *E. coli* 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent *S. cerevisiae* JG 169 cells (OD600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80 μl aliquots were plated on SC+glucose−uracil to give 250–400 c.f.u./plate and incubated at 30° C. for 3–5 days.

Figure 2:
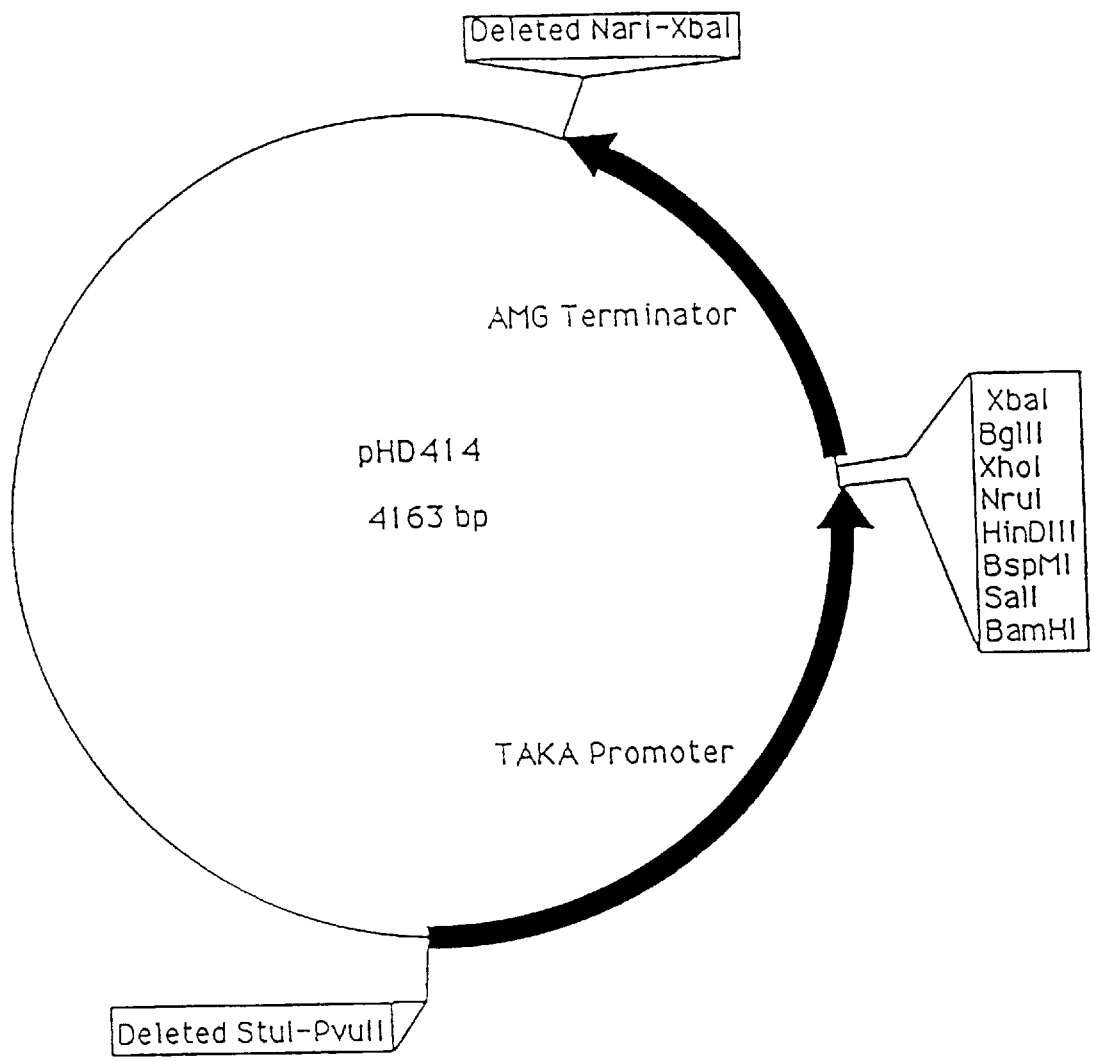
FIG. 2 shows the plasmid pHD414.

Construction of an Aspergillus expression vector: the vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated. The plasmid pHD 414 is shown in FIG. 2.

Media:

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

Pectin overlayer gel: 1% agarose, 1% pectin (DE 35%) in a buffer with an appropriate pH. The gel was boiled and then cooled to 55° C. before the overlayer was poured onto agar plates.

Characterization of an enzyme of the invention:

SDS-PAGE Electrophoresis: SDS-PAGE electrophoresis was performed in a Mini-Leak 4 electrophoresis unit (Kem-En-Tec, Copenhagen) as a modified version of the Laemli procedure [Laemmli, 1970; Christgau, 1991]. Briefly, the separation gel was cast with 12% acrylamide; 0.2% BIS acrylamide; 0.1% SDS; 0.375M Tris pH 8.8; 0.04% APS (ammonium-persulphate) & 0.04% TEMED. After 6–15 hours of polymerization the stacking gel was cast with 4.5% w/w Acrylamide; 0.075% BIS-acrylamide; 0.1% SDS; 66.5 mM Tris pH 6.8; 0.4% w/w APS (ammonium persulphate) & 0.4% TEMED. The electrode chambers are filled with running buffer: 25 mM Tris-base; 0.192M glycine & 0.05% SDS, whereafter the samples containing sample buffer are loaded, and the gel is run at 2–4 mA/gel for over-night running and 10–30 mA/gel for fast running. The gel is subsequently removed and stained by either commassie or silver staining.

Isoelectric focusing: Isoelectric focusing is carried out on Ampholine PAG plates pH 3.5–9.5 (Pharmacia, Upsala) on a Multiphor electrophoresis unit according to the manufactures instructions. After electrophoresis the gel is either commassie stained or silver stained.

Commassie or silver staining: The gel is carefully removed from the glass plates and incubated on a slowly rotating shaking table in approximately 100 ml of the following solutions:

Coomassie staining:
1) 30 min in 40% v/v ethanol; 5% v/v acetic acid
2) 30 min in 40% v/v ethanol; 5% v/v acetic acid+0.1% Commassie R250
3) Destaining in 30 min in 40% v/v ethanol; 5% v/v acetic acid until background is sufficiently reduced.
4) Finally the gel is incubated in preserving solution: 5% v/v acetic acid; 10% v/v ethanol; 5% v/v glycerol and air dried between two sheets of cellophane membrane.

Silver staining:
1) 30 min in 40% v/v ethanol; 5% v/v acetic acid
2) 20 min in 10% v/v ethanol; 5% v/v acetic acid
3) 20 min in 0.0057% w/v APS (0.25 mM)
4) 60 min in 0.1% w/v $AgNO_3$
5) For development, the gel is dipped in developer: 0.015% formaldehyde; 2% w/v $Na_2CO_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

Standard characterization: For standard characterization of the enzyme, incubations are carried out in Eppendorf tubes comprising 1 ml of substrate. The substrate is 75% DE pectin (purified from apple pectin manufactured by Herbstreith KG Pektin Fabrik). When the enzyme is added incubation is carried out at 30° C. and the enzyme is inactivated at 95° C. for 20 minutes. Enzyme incubations are carried out in triplicate. A blank is produced in which enzyme is added but inactivated immediately.

The enzyme activity is determined by measuring the increase in OD at 235 nm during the 15 minutes of incubation compared to the blank. The OD at 235 reflects the amount of unsaturated galacturonic acid produced due to the action of pectin lyase. The extinction coefficient for unsaturated galacturonic acid is $5.55M^{-1}cm^{-1}$.

pH optimum is measured in 0.1M citric acid/tri sodium phosphate buffers of varying pH.

pH stability is measured by leaving the enzyme for 1 hour in 0.1M citric acid/tri sodium phosphate buffers of varying pH before the enzyme is used for incubation at pH 6.0.

Temperature optimum is measured by incubating the enzyme at varying temperatures for 15 minutes.

Temperature stability is measured by leaving the enzyme at various temperatures for 1 and 2 hours before incubation at 30° C.

Substrate stabilisation is measured by leaving the enzyme in the presence of substrate for 1 hour at a suitable temperature before incubation at 30° C.

Km and specific activity are measured by carrying out incubations at different substrate concentrations (S), measure the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

HPLC-SEC: Enzyme incubations for HPLC-SEC analyses are carried out by adding 0.18 μg of enzyme to 1 ml of 1% pectic substrate in 0.1M acetate buffer pH 6.0 and incubate 0, 1, 2, 4 and 24 hours before the enzyme is inactivated. 25 gl of each sample is injected to the SEC columns (three TSK-gel columns connected in a row) and eluted with 0.4M acetate buffer pH 3.0 at 0.8 ml/min supplied by a Dionex pump. Eluting carbohydrates are detected by a refractive index detector (Shimadzu) and the chromatograms are processed by Dionex software. The SEC degradation profile of pectin lyase has been obtained for four different substrates: polygalacturonic acid (Sigma), 35% DE apple pectin purified from apple pectin manufactured by Obipektin AG, 75% DE apple pectin, and Modified Hairy Regions (MHR) obtained from apples by the procedure described by Schols et al, 1990. Dextrans are used as molecular weight standards.

EXAMPLES

Example 1

A library from *A. aculeatus* consisting of approx. $1.5 \times 10^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of plates was then incubated for 2–4 days at 30° C. and overlayered with a pectin overlayer gel for detection of pectinolytic activity. Pectin lyase positive colonies were identified as colonies surrounded by a clearing zone.

Cells from enzyme-positive colonies were spread for single colony isolation on agar, and an enzyme-producing single colony was selected for each of the pectin lyase-producing colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each CDNA clone using the chain-termination method (Sanger et al., 1977) and the Sequenase system (United States Biochemical). The DNA sequence of the enzyme gene is shovn in claim 3.

Isolation of a cDNA gene for expression in Aspergillus: In order to avoid PCR errors in the gene to be cloned, the cDNA was isolated from the yeast plasmid by standard procedures as described below.

One or more of the pectin lyase-producing colonies was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 gl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 μl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 μl TE and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μl/ml.

The DNA was transformed into *E. coli.* by standard procedures. Two *E. coli* colonies were isolated from each of the transformations and analysed with the restriction enzymes HindIII and XbaI which excised the DNA insert. DNA from one of these clones was retransformed into yeast strain JG169.

The DNA sequences of several of the positive clones were partially determined. The partial DNA sequence of the pectin lyase of the invention is shown in claim 3. The full DNA sequence and derived amino acid sequence of the pectin lyase is shown in the Sequence Listing as SEQ ID NO: 35 and SEQ ID NO: 36.

Example 2

In order to express the genes in Aspergillus, cDNA is isolated from one or more representatives of each family by digestion with HindIII/XbaI or other appropriate restriction enzymes, size fractionation on a gel and purification and subsequently ligated to pHD414, resulting in the plasmid PPL-I. After amplification in *E. coli*, the plasmids are transformed into *A. oryzae* or *A. niger* according to the general procedure described below.

Transformation of *Aspergillus oryzae* or *Aspergillus niger* (general procedure)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem. Biophys. Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* transformants

Figure 3:
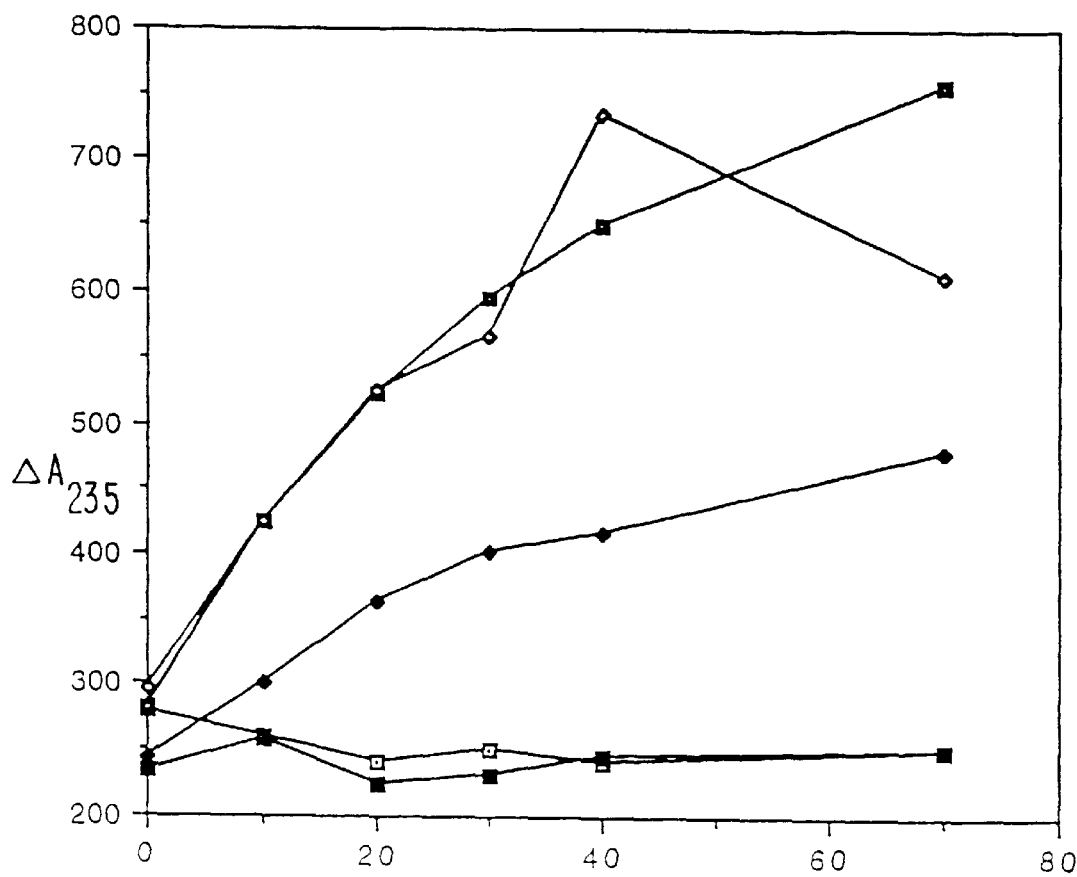
FIG. 3 is a graph showing the pectin lyase activity of a number of different *Aspergillus oryzae* transformants.

Each of the transformants 463A-2, 463A-3, 463A-6 and 463A-13 as well as the control strain 459B-1 (not transformed with a pectin lyase gene) were inoculated in YPD medium. After 5 days of incubation at 30° C., 25 µl of supernatant was added to 10 µl of 1% apple pectin (DE 75) in an appropriate buffer. The mixture was incubated at 30° C. Aliquots were taken at increasing intervals, diluted in water and measured at $A_{235}$. The transformants exhibited a significant increase in $A_{235}$ compared to the control (cf. FIG. 3). This demonstrates efficient expression of pectin lyase in *A. oryzae*.

Example 3
Characterization of a pectin lyase of the invention

The culture supernatant from fermentation of *Aspergillus oryzae* expressing the recombinant enzyme is centrifuged and filtered through a 0.2 µm filter to remove the mycelia. 35–50 ml of the filtered supernatant is ultrafiltrated in a Filtron ultracette or Amicon ultrafiltration device with a 10 kDa membrane to achieve 10 fold concentration. This concentrate is diluted 100 times in 20 mM Tris pH 8.0 in two successive rounds of ultrafiltration in the same device and the supernatant is concentrated to a final volume of 50 ml. This ultrafiltratred sample is loaded at 2 ml/min on a Pharmacia HR16/10 Fast Flow Q Sepharose anion exchanger equilibrated in 20 mM Tris pH 8.0. After the sample has been applied, the column is washed with two column volumes 20 mM Tris pH 8.0, and bound proteins are eluted with a linear increasing NaCl gradient from 0 to 0.6M NaCl in 20 mM Tris pH 8.0. The pectin lyase elutes at approximately 0.3–0.4M NaCl, and fractions containing pectin lyase activity are pooled and concentrated by ultrafiltration. These fractions contain some Aspergillus amylase (α-1.4-glucanase), and in order to achieve complete purification this material is ultrafiltrated in an Amicon ultrafiltration device with a 10 kDa membrane to achieve 10 fold concentration. The concentrate is diluted 100 times in 20 mM Tris pH 7.0 in two successive round of ultrafiltration in the same device. The ultrafiltrated sample is loaded at 1 ml/min onto a HR5/10 Mono Q anion exchange column (Pharmacia, Uppsala) equilibrated in 20 mM Tris, pH 7.0. The column is washed with two column volumes of 20 mM Tris, pH 7.0, and bound proteins are eluted with a linear increasing salt gradient from 0 to 0.4M NaCl in Tris, pH 7.0. The pectin lyase elutes at approximately 0.15M NaCl. The pectin lyase in this fraction is more than 95% pure.

The purified pectin lyase is subsequently characterized with respect to molecular weight, isoelectric point, pH optimum, pH stability, temperature optimum and temperature stability, substrate stabilization, buffer influence, $K_m$ and specific activity. Furthermore the degradation pattern of the enzyme on different pectic substrates has been investigated by HPLC Size Exclusion Chromatography.

Figure 4A:
FIG. 4a shows the molecular weight of the pectin lyase, when analyzed on a silver-stained SDS-PAGE gel.
Figure 4B:
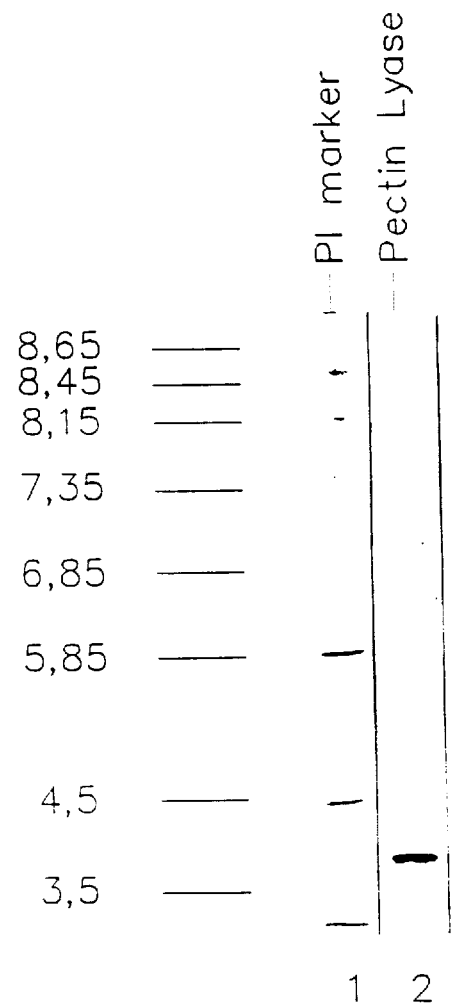
FIG. 4b shows the pI of the pectin lyase when analyzed on a Coomasie stained IEF gel.
Figure 5:
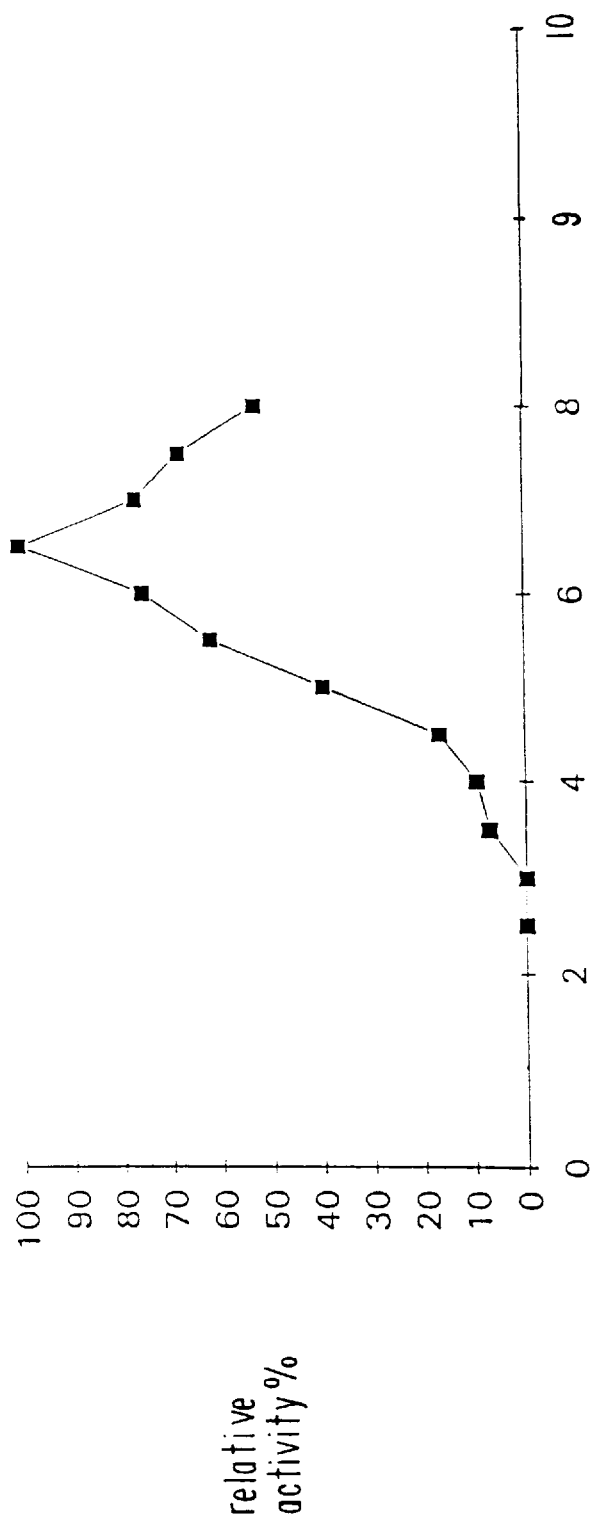
FIG. 5 is a graph showing the relative activity of the pectin lyase at varous pH.
Figure 6:
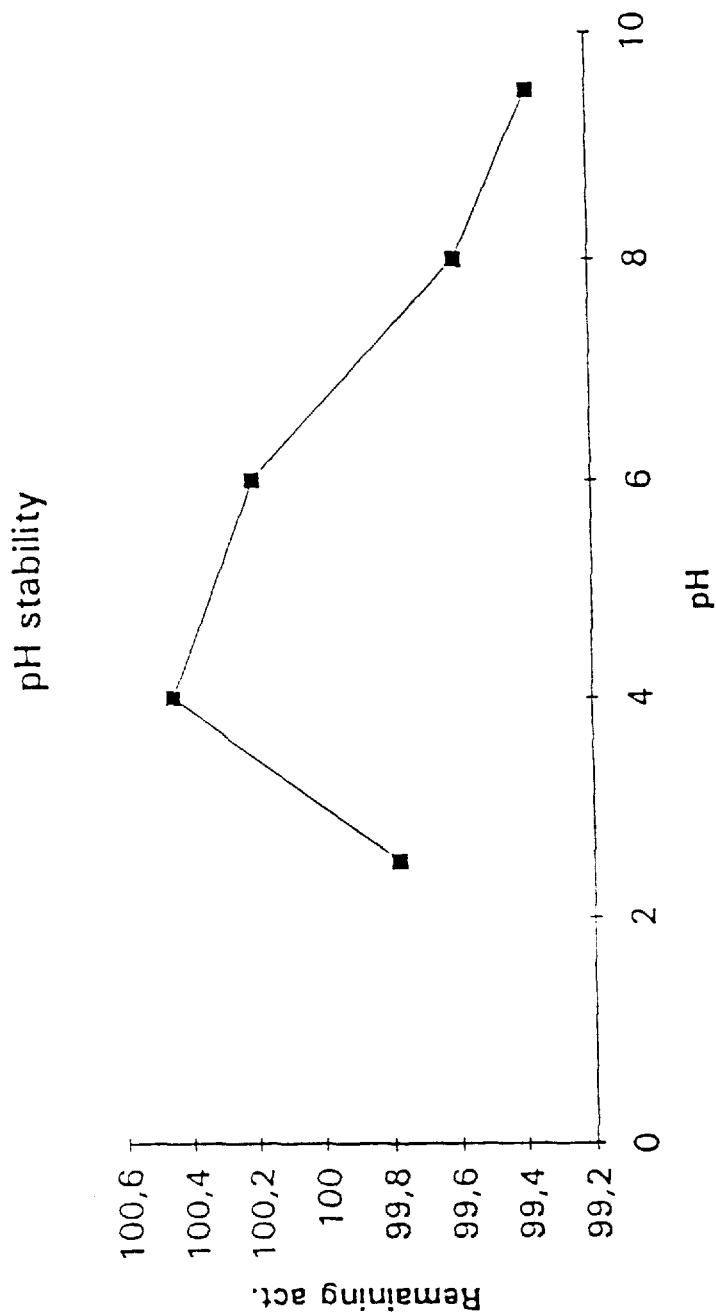
FIG. 6 is a graph showing the pH stability of the pectin lyase.
Figure 7:
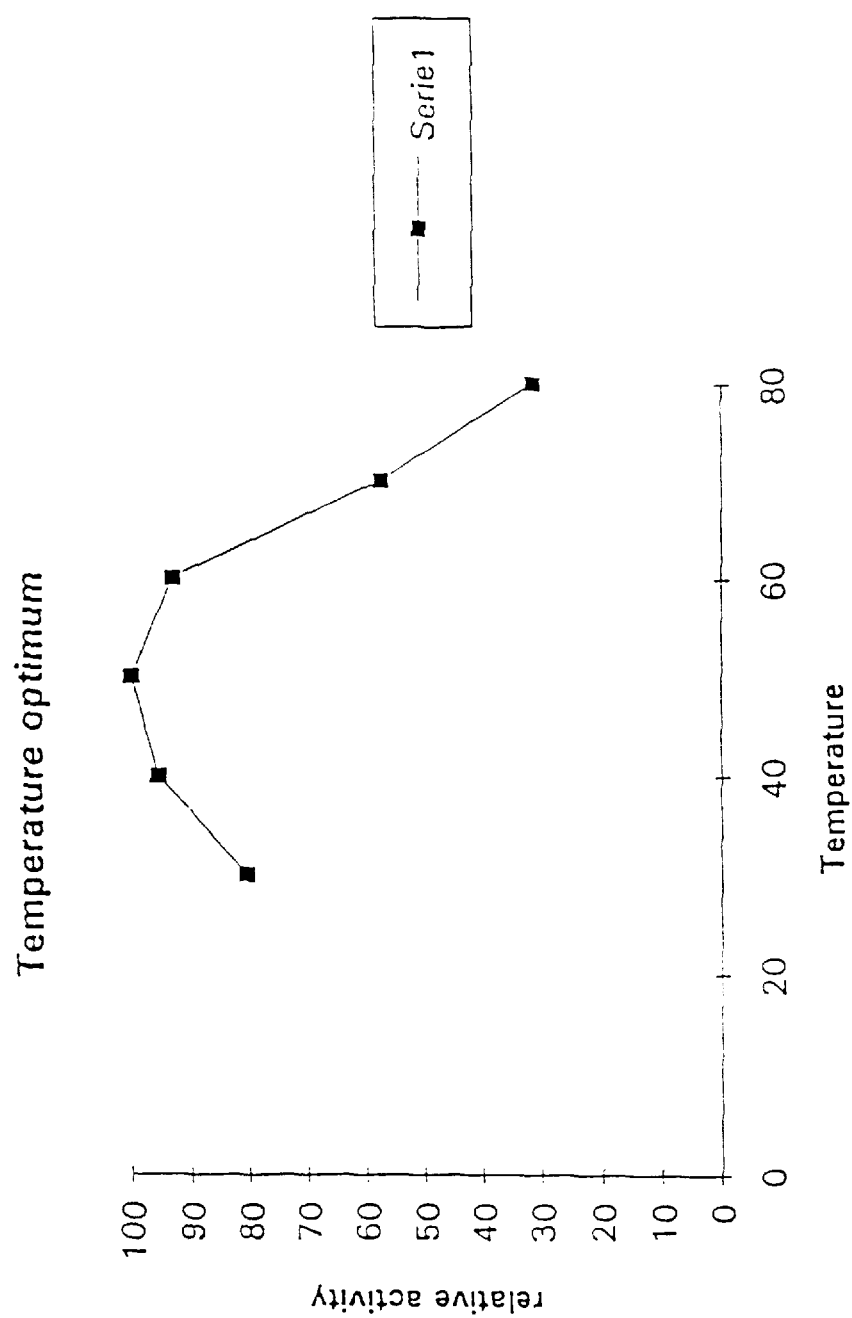
FIG. 7 is a graph showing the temperature optimum of the pectin lyase.
Figure 8:
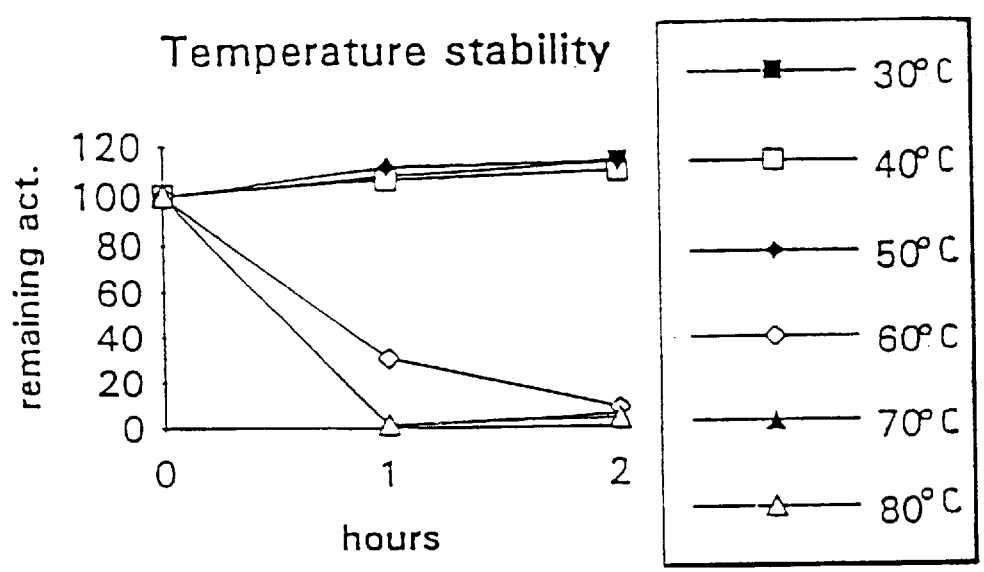
FIG. 8 is a graph showing the temperature stability of the pectin lyase.

More specifically, the purified enzyme was subjected to SDS-PAGE analysis and isoelectric focusing as described above. The resulting molecular characterization of the pectin lyase is illustrated in FIG. 4a and 4b. FIG. 4a illustrates the result of a silver stained SDS-PAGE gel. FIG. 4b illustrates the result of a Coomassie stained IEF gel. The enzyme has a molecular weight of 42 kD as estimated from SDS-PAGE gels, and an isoelectric point of 3.9.

The pH optimum, pH stability, temperature optimum and temperature stability of the purified enzyme were determined as described above and the results are apparent from FIGS. 5 to 8, respectively. The enzyme has a pH optimum in the range of 4.5–8.5, exhibits an acceptable stability in the pH range 2–8 and a temperature in the range of 30°–50° C., and has a temperature optimum in the range of 30°–60° C.

The stability of the enzyme in water and in combination with substrate, respectively, was determined as described in the Materials and Methods section above. The enzyme was found to by unstable in water whereas about 41% of the enzyme activity remained when the enzyme was combined with substrate.

Figure 9:
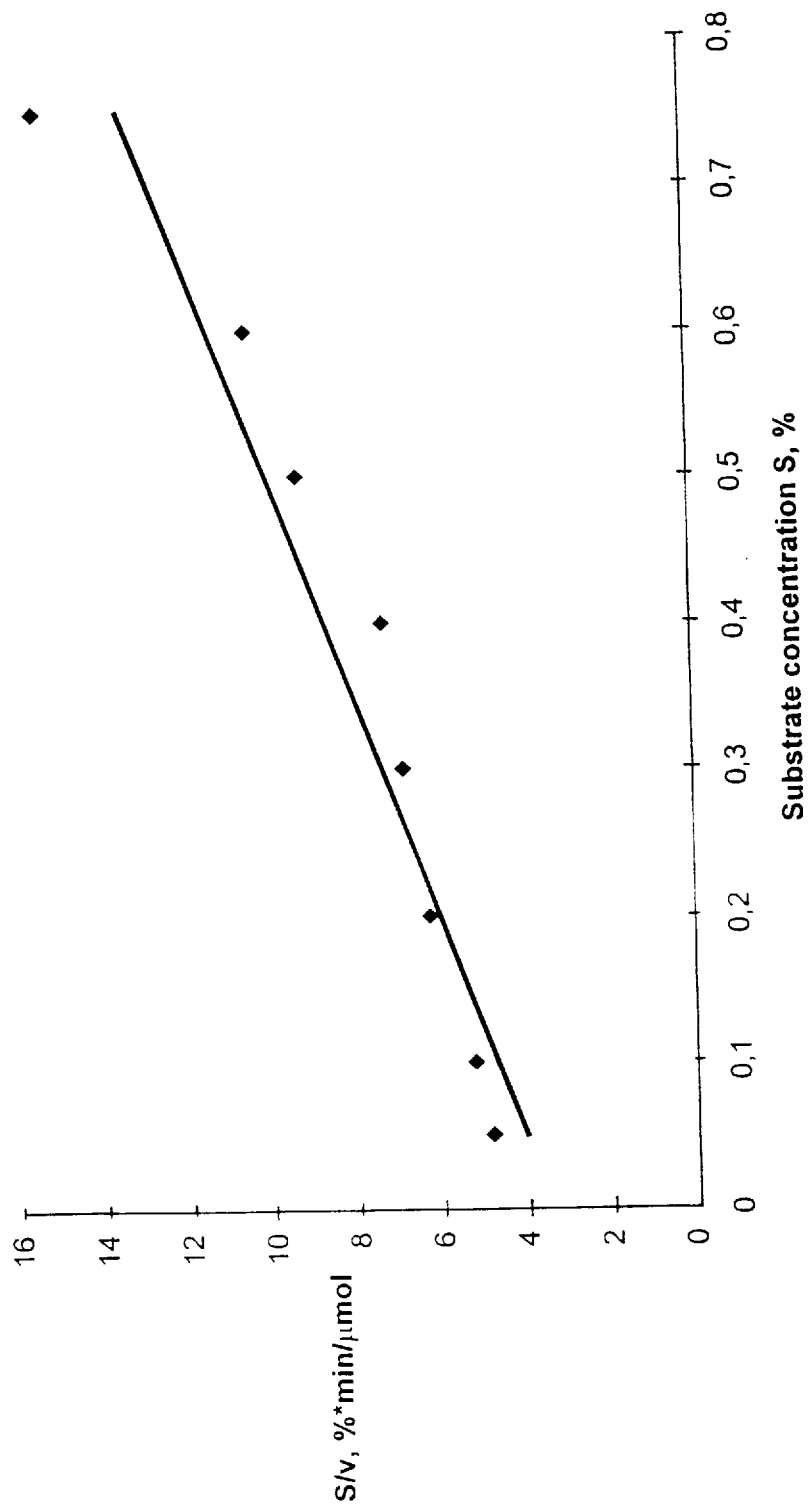
FIG. 9 is a graph showing the $K_m$ and $V_{max}$ of the pectin lyase.

FIG. 9 illustrates the plot of the substrate concentration divided by the hydrolysis velocity (S/v) as a function of the substrated concentration (S) used in determining $K_m$ and the specific activity. Km was determined to 0.163–0.354% 75% DE ($K_m$ expressed as % substrate) apple pectin and the specific activity to 35–50 µmol/min/mg enzyme protein.

The degradation pattern obtained from reaction with the purified pectin lyase was determined by a HPLC-SEC analysis performed as described in the Materials and Methods section above. It was observed that the pectin lyase does not degrade polygalacturonic acid and MHR, that 35% DE pectin is degraded to a limited extent only, and that 75% DE pectin is degraded to a large extent. The limiting oligomer is a dimer indicating that a tetramer is the smallest substrate to be degraded. For 75% DE pectin a substantial amount remains as partly degraded polymeric material, which indicate that the pectin lyase requires a high degree of methyl esterification in order to act.

Example 4

Applications

Apples were homogenized to produce a mash. After thermostating the mash to 20° C., The pectin lyase of example 3 was added in an amount of 100 μg/l and the viscosity was measured by means of a Brookfiled viscosimeter. The viscosity was reduced to 50% in 15 minutes compared to a control with no enzyme added, after which no further viscosity reduction took place. The results show that addition of single-component pectin lyase to apple mash results in a controlled, limited viscosity reduction.

Freshly pressed orange juice, pasteurized orange juice or orange juice rediluted from a concentrate were thermostated to 45° C., and the pectin lyase of example 3 was added to a concentration of 0.2–1.0 g/ton. The viscosity and turbidity of the juice was measured by means of a Brookfield viscosimeter and Lange turbidity meter. The viscosity was reduced to 50% compared to a control with no enzyme added, whereas the turbidity was unchanged. Reconcentrating the enzyme-treated juice resulted in a concentrate at 65° Brix which had a reduced viscosity compared to a sample which had not been treated with the enzyme.

The results show that addition of pectin lyase to orange juice or an orange juice concentrate leads to a controlled, limited viscosity reduction without affecting cloud stability as determined by the turbidity measurement. Furthermore, pectin lyase treated orange juice may be concentrated to higher concentrations without gellification or to a conventional concentration (65° Brix) with a lower viscosity.

REFERENCES

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Christgau, S., et al., 1991, "Pancreatic β-cells express two autoantigenic forms of glutamic acid decarboxylase, a 65 kDa hydrophilic form and a 64 kDa amphiphilic form which can be both membrane-bound and soluble.". J. Biol. Chem., 266, p. 21157–212664.

Schols, H. A. et al., Structural features of Hairy Regions of Pectins isolated from Apple Juice produced by the Liquefaction Process, Carbohydrate Research, 206, pp. 117–129, 1990.

Laemmli, U. K., 1970, "Cleavage of structural proteins during the assembly of the head of bacteriophage T4", Nature, 227, p. 680–685.

We claim:

1. An isolated and purified enzyme exhibiting pectin lyase activity, derived from *Aspergillus aculeatus* encoded by the DNA sequence of SEQ ID NO:35, or a fragment thereof, wherein said fragment encodes a polypeptide having pectin lyase activity.

2. A recombinant expression vector comprising a DNA sequence encoding the enzyme of claim 1.

3. A cell comprising the recombinant expression vector of claim 2.

4. The cell of claim 3, wherein the cell is a eukaryotic cell.

5. The cell of claim 3, wherein the eukaryotic cell is a fungal cell.

6. The cell of claim 5, wherein the fungal cell is a yeast or a filamentous fungal cell.

7. The cell of claim 6, wherein the cell is derived from a strain of Aspergillus.

8. The cell of claim 7, wherein the cell is derived from *Aspergillus niger* or *Aspergillus oryzae*.

9. A method of producing an enzyme exhibiting pectin lyase activity, comprising culturing the cell of claim 3 under conditions permitting the production of the enzyme, and recovering the enzyme from the culture.

10. An enzyme preparation useful for the degradation of plant cell wall components comprising the enzyme of claim 1.

11. The enzyme preparation of claim 10, further comprising one or more enzymes selected from the group consisting of polygalacturonase, pectate lyase and pectin methylesterase.

* * * * *

UNITED STATES PATENT AND TRADEMARK OFFICE
CERTIFICATE OF CORRECTION

PATENT NO.    : 5,858,760

DATED         : January 12, 1999

INVENTOR(S)   : Dalbøge et al.

It is certified that error appears in the above-identified patent and that said Letters Patent is hereby corrected as shown below:

Col. 6, line 54, delete "GUSCN" and insert --GuSCN--;

Col. 12, line 15, delete "CDNA" and insert -cDNA--;

Col. 13, line 4, delete "PPL-I" and insert --pPL-I;

Col. 32, line 66, in Claim 5, delete "claim 3" and insert --claim 4--.

Signed and Sealed this

Twenty-third Day of November, 1999

Attest:

Q. TODD DICKINSON

Attesting Officer    Acting Commissioner of Patents and Trademarks

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGATAAACTG CAATATGGCA         2 0

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TTGACCACGA TGGCTCAGGT         2 0

( 2 ) INFORMATION FOR SEQ ID NO: 3:

( i ) SEQUENCE CHARACTERISTICS:

(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 3:

CTTTGGCCGT TGGCCCAGCT 20

(2) INFORMATION FOR SEQ ID NO: 4:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 4:

CGCCACAGCT GTGAGTGTTT 20

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 5:

CCGGTGCGGC AGAGGGCTTC 20

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 6:

GCAAAAGGTG TCACTGGTGG 20

(2) INFORMATION FOR SEQ ID NO: 7:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 7:

TGGTAGTGCG ACTCCGGTTT 20

(2) INFORMATION FOR SEQ ID NO: 8:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 8:

ATCTACCACG ACTGATGAGC 20

(2) INFORMATION FOR SEQ ID NO: 9:

(i) SEQUENCE CHARACTERISTICS:
(A) LENGTH: 24 base pairs
(B) TYPE: nucleic acid ( C ) STRANDEDNESS: single
( D ) TOPOLOGY: linear ( x i ) SEQUENCE DESCRIPTION: SEQ ID NO: 9:

TGGTCTCCTA CCTCGGTGAC TCTT  24

( 2 ) INFORMATION FOR SEQ ID NO: 10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 10:

GCATTGTCAG CGGTGCCAGC  20

( 2 ) INFORMATION FOR SEQ ID NO: 11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 11:

AATATTATCA TTCAGAACGT  20

( 2 ) INFORMATION FOR SEQ ID NO: 12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 12:

CGCAATTACA GATATCAACG  20

( 2 ) INFORMATION FOR SEQ ID NO: 13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 13:

AGAAATACGT CTGGGGTGGT  20

( 2 ) INFORMATION FOR SEQ ID NO: 14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 14:

GATGCCATCA CCCTCGACGA  20

( 2 ) INFORMATION FOR SEQ ID NO: 15:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear (x i) SEQUENCE DESCRIPTION: SEQ ID NO: 15:

CGCCGATATG GTCTGGATCG                                                            20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 16:

ACCATGTTAC GACCGCCCGC                                                            20

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 17:

ATCGGCCGCC AGCACGTCGT                                                            20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 18:

CCTCGGCACA AGCGCCGACA                                                            20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 19:

ACCGCGTCAC CATCTCCAAC                                                            20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 20:

TCGTACTTCA ACGGTGTCAC                                                            20

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO: 21:

CAGTCACAGC GCAACGTGTG ACGG 24

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 22:

TTGTCGCAGT CCGACACCGC 20

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 23:

TTTCTTGGTC AACTTTGAAG 20

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 24:

GCAAGAATAT GCGACCGTCG 20

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 25:

TCGGCGTACA CGGCGATCAA 20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 26:

GACTACGGTG CCGAGTAACG 20

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 27:

CGGGCCAGGG TAATCTCTGA 20

( 2 ) INFORMATION FOR SEQ ID NO: 28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

| | |
|---|---:|
| GCGGTTGGCC AGGCTCGAAG | 20 |

( 2 ) INFORMATION FOR SEQ ID NO: 29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

| | |
|---|---:|
| TATGCCTTAC CCTGCCTGGT | 20 |

( 2 ) INFORMATION FOR SEQ ID NO: 30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 30:

| | |
|---|---:|
| GGCAAGTAGC ACTTGAGAGC | 20 |

( 2 ) INFORMATION FOR SEQ ID NO: 31:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 31:

| | |
|---|---:|
| TCACTGCAAC GG | 12 |

( 2 ) INFORMATION FOR SEQ ID NO: 32:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 32:

| | |
|---|---:|
| CGATAAACTG CAATATGGCA TTGACCACGA TGGCTCAGGT CTTTGGCCGT TGGCCCAGCT | 60 |
| CGCCACAGCT GTGAGTGTTT CCGGTGCGGC AGAGGGCTTC GCAAAAGGTG TCACTGGTGG | 120 |
| TGGTAGTGCG ACTCCGGTTT ATCTACCACG ACTGATGAGC TGGTCTCCTA CCTCGGTGAC | 180 |
| TCTT | 184 |

( 2 ) INFORMATION FOR SEQ ID NO: 33:

( i ) SEQUENCE CHARACTERISTICS:
        ( A ) LENGTH: 244 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 33:

GCATTGTCAG CGGTGCCAGC AATATTATCA TTCAGAACGT CGCAATTACA GATATCAACG 60

AGAAATACGT CTGGGGTGGT GATGCCATCA CCCTCGACGA CGCCGATATG GTCTGGATCG 120

ACCATGTTAC GACCGCCCGC ATCGGCCGCC AGCACGTCGT CCTCGGCACA AGCGCCGACA 180

ACCGCGTCAC CATCTCCAAC TCGTACTTCA ACGGTGTCAC CAGTCACAGC GCAACGTGTG 240

ACGG 244

( 2 ) INFORMATION FOR SEQ ID NO: 34:

( i ) SEQUENCE CHARACTERISTICS:
        ( A ) LENGTH: 192 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 34:

TTGTCGCAGT CCGACACCGC TTTCTTGGTC AACTTTGAAG GCAAGAATAT GCGACCGTCG 60

TCGGCGTACA CGGCGATCAA GACTACGGTG CCGAGTAACG CGGGCCAGGG TAATCTCTGA 120

GCGGTTGGCC AGGCTCGAAG TATGCCTTAC CCTGCCTGGT GGCAAGTAGC ACTTGAGAGC 180

TCACTGCAAC GG 192

( 2 ) INFORMATION FOR SEQ ID NO: 35:

( i ) SEQUENCE CHARACTERISTICS:
        ( A ) LENGTH: 1291 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 15..1151

( x i ) SEQUENCE DESCRIPTION: SEQ ID NO: 35:

```
CGATAAACTG CAAT ATG GCA TTG ACC ACG ATT CTC AGT CTT TTG GCC GTT      50
               Met Ala Leu Thr Thr Ile Leu Ser Leu Leu Ala Val
                1               5                   10

GCC GCC CAG CTC GCC ACA GCT GTG AGT GTT TCC GGT GCG GCA GAG GGC      98
Ala Ala Gln Leu Ala Thr Ala Val Ser Val Ser Gly Ala Ala Glu Gly
            15                  20                  25

TTC GCA AAA GGT GTC ACT GGT GGT GGT AGT GCG ACT CCG GTT TAT CCT     146
Phe Ala Lys Gly Val Thr Gly Gly Gly Ser Ala Thr Pro Val Tyr Pro
        30                  35                  40

ACC ACG ACT GAT GAG CTG GTC TCC TAC CTC GGT GAC TCT TCG GCG CGA     194
Thr Thr Thr Asp Glu Leu Val Ser Tyr Leu Gly Asp Ser Ser Ala Arg
 45                 50                  55                  60

GTG ATC GTT CTC CAG CAG ACC TTT GAC TTC ACC GGC ACT GAG GGT ACC     242
Val Ile Val Leu Gln Gln Thr Phe Asp Phe Thr Gly Thr Glu Gly Thr
                65                  70                  75

ACT ACG GCC ACC GGA TGT GCA CCA TGG ACC ACT GCT AGT GGC TGC CAG     290
Thr Thr Ala Thr Gly Cys Ala Pro Trp Thr Thr Ala Ser Gly Cys Gln
            80                  85                  90

CTC GCC ATT AAC CAG AAT GAC TGG TGT ACG AAC TAT GAG CCC GAC GCT     338
Leu Ala Ile Asn Gln Asn Asp Trp Cys Thr Asn Tyr Glu Pro Asp Ala
        95                  100                 105

CCA AGT GTC TCC GTG ACA TAC GAT AAC GCT GGT GTG CTG GGT ATC ACT     386
Pro Ser Val Ser Val Thr Tyr Asp Asn Ala Gly Val Leu Gly Ile Thr
    110                 115                 120

GTC GCA TCG GAC AAG ACC CTT ATC GGC GTG GGA TCC ACC GGC ATC ATC     434
```

| | | | | | | | | | | | | | | | | |
|---|---|---|---|---|---|---|---|---|---|---|---|---|---|---|---|---|
| Val | Ala | Ser | Asp | Lys | Thr | Leu | Ile | Gly | Val | Gly | Ser | Thr | Gly | Ile | Ile | |
| 125 | | | | 130 | | | | | 135 | | | | | | 140 | |
| AAG | GGC | AAG | GGT | CTT | CGC | ATT | GTC | AGC | GGT | GCC | AGC | AAT | ATT | ATC | ATT | 482 |
| Lys | Gly | Lys | Gly | Leu | Arg | Ile | Val | Ser | Gly | Ala | Ser | Asn | Ile | Ile | Ile | |
| | | | | 145 | | | | | 150 | | | | | 155 | | |
| CAG | AAC | GTC | GCA | ATT | ACA | GAT | ATC | AAC | GAG | AAA | TAC | GTC | TGG | GGT | GGT | 530 |
| Gln | Asn | Val | Ala | Ile | Thr | Asp | Ile | Asn | Glu | Lys | Tyr | Val | Trp | Gly | Gly | |
| | | | 160 | | | | | 165 | | | | | 170 | | | |
| GAT | GCC | ATC | ACC | CTC | GAC | GAC | GCC | GAT | ATG | GTC | TGG | ATC | GAC | CAT | GTT | 578 |
| Asp | Ala | Ile | Thr | Leu | Asp | Asp | Ala | Asp | Met | Val | Trp | Ile | Asp | His | Val | |
| | | 175 | | | | | 180 | | | | | 185 | | | | |
| ACG | ACC | GCC | CGC | ATC | GGC | CGC | CAG | CAC | GTC | GTC | CTC | GGC | ACA | AGC | GCC | 626 |
| Thr | Thr | Ala | Arg | Ile | Gly | Arg | Gln | His | Val | Val | Leu | Gly | Thr | Ser | Ala | |
| | 190 | | | | | 195 | | | | | 200 | | | | | |
| GAC | AAC | CGC | GTC | ACC | ATC | TCC | AAC | TCG | TAC | TTC | AAC | GGT | GTC | ACC | AGC | 674 |
| Asp | Asn | Arg | Val | Thr | Ile | Ser | Asn | Ser | Tyr | Phe | Asn | Gly | Val | Thr | Ser | |
| 205 | | | | | 210 | | | | | 215 | | | | | 220 | |
| TAC | AGC | GCA | ACG | TGT | GAC | GGC | TAC | GCA | TAC | TGG | GGT | TTA | TAC | TTC | GAC | 722 |
| Tyr | Ser | Ala | Thr | Cys | Asp | Gly | Tyr | Ala | Tyr | Trp | Gly | Leu | Tyr | Phe | Asp | |
| | | | | 225 | | | | | 230 | | | | | 235 | | |
| GGC | TCG | TCC | GAC | CTG | GTC | ACC | CTC | CAG | AAG | AAT | TAC | ATC | TAT | CAC | TTC | 770 |
| Gly | Ser | Ser | Asp | Leu | Val | Thr | Leu | Gln | Lys | Asn | Tyr | Ile | Tyr | His | Phe | |
| | | | 240 | | | | | 245 | | | | | 250 | | | |
| AGC | GGC | CGG | AGC | CCG | AAG | GTC | CAG | GGC | AAC | ACC | CTT | CTA | CAC | GCC | GTC | 818 |
| Ser | Gly | Arg | Ser | Pro | Lys | Val | Gln | Gly | Asn | Thr | Leu | Leu | His | Ala | Val | |
| | | 255 | | | | | 260 | | | | | 265 | | | | |
| AAC | AAC | TAC | TGG | TAC | GAC | TCC | GAC | GGC | CAC | TCG | TTC | GAG | ATT | GGC | AGT | 866 |
| Asn | Asn | Tyr | Trp | Tyr | Asp | Ser | Asp | Gly | His | Ser | Phe | Glu | Ile | Gly | Ser | |
| | 270 | | | | | 275 | | | | | 280 | | | | | |
| GGG | GGC | TAC | GTG | CTG | GCC | GAA | GGC | AAC | GTC | TTC | CAG | AAC | ATC | GAC | ACT | 914 |
| Gly | Gly | Tyr | Val | Leu | Ala | Glu | Gly | Asn | Val | Phe | Gln | Asn | Ile | Asp | Thr | |
| 285 | | | | | 290 | | | | | 295 | | | | | 300 | |
| CCC | GTC | GAA | TCT | CCG | GTG | TCG | GGA | CAG | CTG | TTC | ACC | TCC | CCC | GAC | TCG | 962 |
| Pro | Val | Glu | Ser | Pro | Val | Ser | Gly | Gln | Leu | Phe | Thr | Ser | Pro | Asp | Ser | |
| | | | | 305 | | | | | 310 | | | | | 315 | | |
| ACG | ACC | AAC | GCA | GTC | TGC | TCG | ACC | TAC | CTT | GGC | CGC | GCG | TGC | CAG | ATC | 1010 |
| Thr | Thr | Asn | Ala | Val | Cys | Ser | Thr | Tyr | Leu | Gly | Arg | Ala | Cys | Gln | Ile | |
| | | | 320 | | | | | 325 | | | | | 330 | | | |
| AAC | GGG | TTC | GGG | AGC | TCG | GGC | ACC | TTC | TCG | CAG | TCC | GAC | ACC | GCT | TTC | 1058 |
| Asn | Gly | Phe | Gly | Ser | Ser | Gly | Thr | Phe | Ser | Gln | Ser | Asp | Thr | Ala | Phe | |
| | | 335 | | | | | 340 | | | | | 345 | | | | |
| TTG | GTC | AAC | TTT | GAA | GGC | AAG | AAT | ATC | GCG | ACC | GCG | TCG | GCG | TAC | ACG | 1106 |
| Leu | Val | Asn | Phe | Glu | Gly | Lys | Asn | Ile | Ala | Thr | Ala | Ser | Ala | Tyr | Thr | |
| | 350 | | | | | 355 | | | | | 360 | | | | | |
| GCG | ATC | AAG | ACT | ACG | GTG | CCG | AGT | AAC | GCG | GGC | CAG | GGT | AAT | CTC | | 1151 |
| Ala | Ile | Lys | Thr | Thr | Val | Pro | Ser | Asn | Ala | Gly | Gln | Gly | Asn | Leu | | |
| 365 | | | | | 370 | | | | | 375 | | | | | | |

TGAGCGGTTG GCCAGGCTCG AAGTATGCCT TACCCTGCCT GGTGGCAAAG TAGCACTTGA 1211

GAGGCTATGG AACGGGAGCA GCCAGATAGC TAGCTAGGAA TAGGATATAT GCACATCTTA 1271

AAAAAAAAAA AAAAAAAAA 1291

( 2 ) INFORMATION FOR SEQ ID NO: 36:

( i ) SEQUENCE CHARACTERISTICS:
        ( A ) LENGTH: 379 amino acids
        ( B ) TYPE: amino acid
        ( D ) TOPOLOGY: linear ( x i ) SEQUENCE DESCRIPTION: SEQ ID NO: 36:

Met Ala Leu Thr Thr Ile Leu Ser Leu Leu Ala Val Ala Ala Gln Leu

|  |  |  |  |  |  |  |  |  |  |  |  |  |  |  |
|---|---|---|---|---|---|---|---|---|---|---|---|---|---|---|
| 1 |  |  |  | 5 |  |  |  |  | 10 |  |  |  |  | 15 |
| Ala | Thr | Ala | Val | Ser | Val | Ser | Gly | Ala | Ala | Glu | Gly | Phe | Ala | Lys | Gly |
|  |  |  | 20 |  |  |  |  | 25 |  |  |  |  | 30 |  |
| Val | Thr | Gly | Gly | Gly | Ser | Ala | Thr | Pro | Val | Tyr | Pro | Thr | Thr | Asp |
|  |  | 35 |  |  |  |  | 40 |  |  |  |  | 45 |  |  |
| Glu | Leu | Val | Ser | Tyr | Leu | Gly | Asp | Ser | Ser | Ala | Arg | Val | Ile | Val | Leu |
|  | 50 |  |  |  |  | 55 |  |  |  |  | 60 |  |  |  |
| Gln | Gln | Thr | Phe | Asp | Phe | Thr | Gly | Thr | Glu | Gly | Thr | Thr | Thr | Ala | Thr |
| 65 |  |  |  |  | 70 |  |  |  |  | 75 |  |  |  |  | 80 |
| Gly | Cys | Ala | Pro | Trp | Thr | Thr | Ala | Ser | Gly | Cys | Gln | Leu | Ala | Ile | Asn |
|  |  |  |  | 85 |  |  |  |  | 90 |  |  |  |  | 95 |  |
| Gln | Asn | Asp | Trp | Cys | Thr | Asn | Tyr | Glu | Pro | Asp | Ala | Pro | Ser | Val | Ser |
|  |  |  |  | 100 |  |  |  |  | 105 |  |  |  |  | 110 |  |
| Val | Thr | Tyr | Asp | Asn | Ala | Gly | Val | Leu | Gly | Ile | Thr | Val | Ala | Ser | Asp |
|  |  |  | 115 |  |  |  |  | 120 |  |  |  |  | 125 |  |  |
| Lys | Thr | Leu | Ile | Gly | Val | Gly | Ser | Thr | Gly | Ile | Ile | Lys | Gly | Lys | Gly |
|  |  | 130 |  |  |  |  | 135 |  |  |  |  | 140 |  |  |  |
| Leu | Arg | Ile | Val | Ser | Gly | Ala | Ser | Asn | Ile | Ile | Ile | Gln | Asn | Val | Ala |
| 145 |  |  |  |  |  | 150 |  |  |  |  | 155 |  |  |  | 160 |
| Ile | Thr | Asp | Ile | Asn | Glu | Lys | Tyr | Val | Trp | Gly | Gly | Asp | Ala | Ile | Thr |
|  |  |  |  | 165 |  |  |  |  | 170 |  |  |  |  | 175 |  |
| Leu | Asp | Asp | Ala | Asp | Met | Val | Trp | Ile | Asp | His | Val | Thr | Thr | Ala | Arg |
|  |  |  | 180 |  |  |  |  | 185 |  |  |  |  | 190 |  |  |
| Ile | Gly | Arg | Gln | His | Val | Val | Leu | Gly | Thr | Ser | Ala | Asp | Asn | Arg | Val |
|  |  | 195 |  |  |  |  | 200 |  |  |  |  | 205 |  |  |  |
| Thr | Ile | Ser | Asn | Ser | Tyr | Phe | Asn | Gly | Val | Thr | Ser | Tyr | Ser | Ala | Thr |
|  | 210 |  |  |  |  | 215 |  |  |  |  | 220 |  |  |  |  |
| Cys | Asp | Gly | Tyr | Ala | Tyr | Trp | Gly | Leu | Tyr | Phe | Asp | Gly | Ser | Ser | Asp |
| 225 |  |  |  |  | 230 |  |  |  |  | 235 |  |  |  |  | 240 |
| Leu | Val | Thr | Leu | Gln | Lys | Asn | Tyr | Ile | Tyr | His | Phe | Ser | Gly | Arg | Ser |
|  |  |  |  | 245 |  |  |  |  | 250 |  |  |  |  | 255 |  |
| Pro | Lys | Val | Gln | Gly | Asn | Thr | Leu | Leu | His | Ala | Val | Asn | Asn | Tyr | Trp |
|  |  |  | 260 |  |  |  |  | 265 |  |  |  |  | 270 |  |  |
| Tyr | Asp | Ser | Asp | Gly | His | Ser | Phe | Glu | Ile | Gly | Ser | Gly | Gly | Tyr | Val |
|  |  | 275 |  |  |  |  | 280 |  |  |  |  | 285 |  |  |  |
| Leu | Ala | Glu | Gly | Asn | Val | Phe | Gln | Asn | Ile | Asp | Thr | Pro | Val | Glu | Ser |
|  | 290 |  |  |  |  | 295 |  |  |  |  | 300 |  |  |  |  |
| Pro | Val | Ser | Gly | Gln | Leu | Phe | Thr | Ser | Pro | Asp | Ser | Thr | Thr | Asn | Ala |
| 305 |  |  |  |  | 310 |  |  |  |  | 315 |  |  |  |  | 320 |
| Val | Cys | Ser | Thr | Tyr | Leu | Gly | Arg | Ala | Cys | Gln | Ile | Asn | Gly | Phe | Gly |
|  |  |  |  | 325 |  |  |  |  | 330 |  |  |  |  | 335 |  |
| Ser | Ser | Gly | Thr | Phe | Ser | Gln | Ser | Asp | Thr | Ala | Phe | Leu | Val | Asn | Phe |
|  |  |  | 340 |  |  |  |  | 345 |  |  |  |  | 350 |  |  |
| Glu | Gly | Lys | Asn | Ile | Ala | Thr | Ala | Ser | Ala | Tyr | Thr | Ala | Ile | Lys | Thr |
|  |  | 355 |  |  |  |  | 360 |  |  |  |  | 365 |  |  |  |
| Thr | Val | Pro | Ser | Asn | Ala | Gly | Gln | Gly | Asn | Leu |  |  |  |  |  |
|  | 370 |  |  |  |  | 375 |  |  |  |  |  |  |  |  |  |